United States Patent [19]

Gilman

[11] Patent Number: 5,018,515

[45] Date of Patent: May 28, 1991

[54] SEE THROUGH ABSORBENT DRESSING

[75] Inventor: Thomas Gilman, Lake Zurich, Ill.

[73] Assignee: The Kendall Company, Mansfield, Mass.

[21] Appl. No.: 132,435

[22] Filed: Dec. 14, 1987

[51] Int. Cl.⁵ .............................................. A61L 15/00
[52] U.S. Cl. ...................................... 128/155; 128/156; 604/358
[58] Field of Search ............... 128/155, 156; 604/304, 604/307, 375, 370, 372, 364, 378, 383, 358, 360; 5/485, 502

[56] References Cited

U.S. PATENT DOCUMENTS

| | | | |
|---|---|---|---|
| 3,307,545 | 3/1967 | Surowitz | 128/156 |
| 3,416,525 | 12/1968 | Yeremian | 128/156 |
| 3,438,371 | 4/1969 | Fischer et al. | 128/156 |
| 4,231,357 | 11/1980 | Hessner | 128/156 |
| 4,545,371 | 10/1985 | Grossman et al. | 128/155 |

Primary Examiner—David J. Isabella
Assistant Examiner—Paul Prebilic
Attorney, Agent, or Firm—Alvin Isaacs

[57] ABSTRACT

An absorbent dressing comprising, a transparent backing sheet having a relatively high water vapor permeability, a front sheet having a pressure sensitive adhesive on a front surface thereof for facing a wound with the front sheet and adhesive having a plurality of apertures extending therethrough, and an absorbent layer intermediate the front sheet and backing sheet having a plurality of openings in register with the apertures of the front sheet, with the openings of the layer being at least as large as the apertures of the front sheet.

11 Claims, 2 Drawing Sheets

SEE THROUGH ABSORBENT DRESSING

BACKGROUND OF THE INVENTION

The present invention relates to absorbent dressings.

In the past, adhesive coated elastomer film dressings permeable to water vapor for application over a wound of a patient have been known. However, such dressings do not have the attribute of holding and sequestering wound fluid, and they may be adherent to the wound which may disrupt the wound upon removal of the dressing. Also, such dressings do not dissipate fluid that the wound produces, and the seal of the dressing to the skin surrounding the wound may be underminded by the fluid production.

Various dressings or articles are disclosed in U.S. Pat. Nos. 4,499,896, 797,094, 4,592,751, 2,807,262, 4,173,046, and 3,994,299, incorporated herein by reference.

SUMMARY OF THE INVENTION

A principal feature of the present invention is the provision of an improved absorbent dressing.

The dressing of the present invention comprises, a transparent backing sheet having a relatively high water vapor permeability, a front sheet having a pressure sensitive adhesive on a front surface thereof facing a wound, with the front sheet and adhesive having a plurality of apertures extending therethrough, and an absorbent layer intermediate the front sheet and backing sheet having a plurality of openings in register with the apertures of the front sheet, with the openings of the layer being at least as large as the apertures of the front sheet.

A feature of the present invention is that the dressing is not adherent to a wound, since the openings of the layer are at least as large as the apertures of the front sheet, and the layer does not come in contact with the wound during use of the dressing.

Another feature of the invention is that the wound may be visually inspected through the transparent backing sheet, the openings of the layer, and the apertures of the front sheet in order to continuously monitor the condition of the wound during use of the dressing on the wound.

A feature of the present invention is that the dressing need not be replaced during healing of the wound, since the healing condition of the wound may be monitored during use of the dressing.

Yet another feature of the invention is that the fluids from the wound are dissipated into the layer, and do not undermine the adhesive of the dressing surrounding the wound.

Still another feature of the invention is that the backing sheet and front sheet may be sealed around their periphery in order to make the dressing impervious to fluid and microbes, including viruses.

A further feature of the invention is that the dressing may include an adhesive coated margin of the backing sheet to adhere the dressing to a patient's skin over the wound and providing a barrier to the wound.

Still another feature of the invention is that the dressing may include tape strips having water vapor permeable backings to secure the backing sheet to the patient's skin around the periphery of the dressing.

A feature of the invention is the provision of a method and apparatus for making the dressing of the present invention.

Further features will become more fully apparent in the following description of the embodiments of this invention and from the appended claims.

DESCRIPTION OF THE PREFERRED EMBODIMENTS

Figure 1:
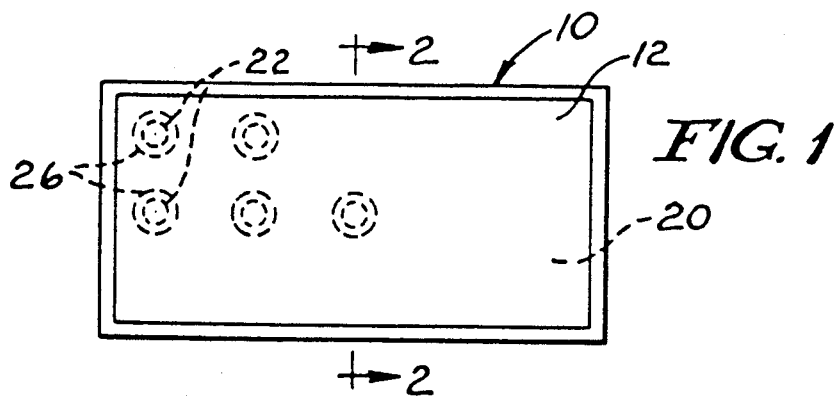
FIG. 1 is a top plan view of an absorbent dressing of the present invention.
Figure 2:
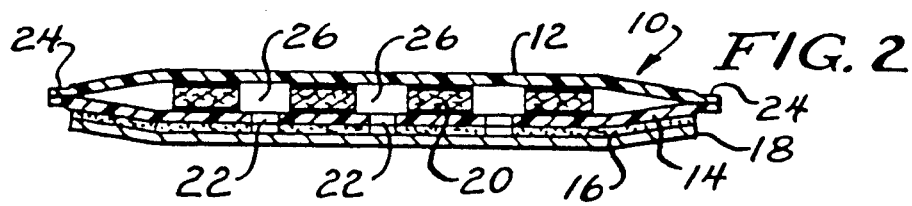
FIG. 2 is a sectional view taken substantially as indicated along the line 2—2 of FIG. 1.
Figure 3:
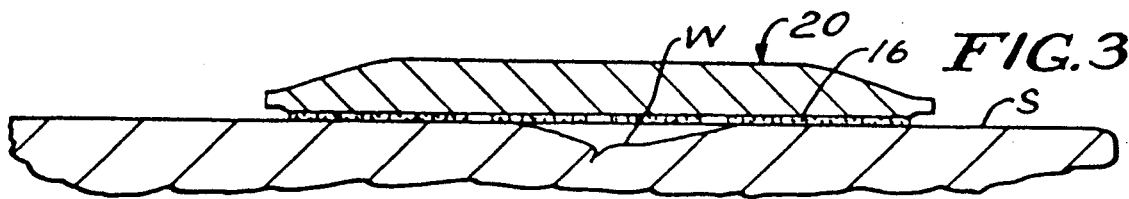
FIG. 3 is a diagrammatic sectional view illustrating use of the dressing over a wound.

Referring now to FIGS. 1-3, there is shown an absorbent dressing generally designated 10 having a backing sheet 12 of an elastomer highly permeable to water vapor such as PEBAX 3533 an elastomer film supplied by Schoeller Technical Papers, Pulaski, N.Y., a nylon/polyether block copolymer. The backing sheet 12 is also transparent for visual inspection of the dressing, as will be described below. The dressing 10 has a front sheet 14 of an elastomer film permeable to water vapor such as Hytrel 4056, a trademark of E.I. Dupont Denemours. The front sheet 14 has a pressure-sensitive adhesive coating 16 on a front surface thereof, such as an acrylic pressure-sensitive adhesive. The front surface of the adhesive coating 16 is releasably covered by a release sheet 18 which may be removed at the time of the use of the dressing 10 for application of the adhesive coating 16 over and around the wound of a patient. The front sheet 14 and adhesive coating 16 have a plurality of apertures 22 disposed throughout the width and length of the dressing extending through the adhesive coating 16 and front sheet 14.

The dressing has a layer 20 of an absorbent material located intermediately the front sheet 14 and backing sheet 12. In this embodiment, the front sheet 14 and backing sheet 12 have a seal line 24 extending around the periphery of the dressing 10 which renders the dressing impervious to the fluid, and also microbes including viruses, such that when the dressing 10 is in place, it provides a complete barrier preventing contamination from outside reaching the wound. The layer 20 may be constructed from a suitable non-woven fabric, such as Novonette, a trademark of the Kendall Company, Boston, Massachusetts, or a needle punched fabric. In the case of the needle punched fabric, the fibers tend to be orientated in the direction perpendicular to the fabric plane, such that the fibers will communicate with both surfaces of the fabric. If a single fiber is thus sealed to both the front sheet 14 and backing sheet 12, it will serve to hold the construction together, and the use of a needle punched fabric in this invention adds stability to the structure. The layer 20 has a plurality of openings 26 in register with the apertures 22 of the front sheet 14 and adhesive coating 16, with the openings 26 being at least as large as the apertures 22, and in a preferred form being larger than the apertures 22. In a preferred form, the backing sheet 12 and front sheet 14 are heat sealed to the layer 20 by suitable techniques known to the art.

In use of the dressing 10, the release sheet 18 is removed from the adhesive coating 16, and the dressing 10 is applied to the patients skin S surrounding the location of the patient wound W. During use, any excess fluid produced by the wound W will enter the dressing 10 through the small openings 22 in the front sheet 14 and adhesive coating 16, and if there is sufficient fluid it will eventually reach the absorbent layer 20 where it is spread laterally to other areas of the layer 20, and held away from the wound surface. The wound fluid is then rapidly evaporated through the backing sheet 12, since the backing sheet 12 has a relatively high moisture vapor transmission rate, and since the fluid is exposed to a relatively large area of the backing sheet 12.

Although absorbent, the dressing 10 is non-adherent to the wound surface, since the absorbent layer 20 is at no point in contact with the wound surface due to the relative size of the openings 26 and apertures 22 in the layer 20 and is not subject to tissue ingrowth. The dressing 10 is self adherent, due to the coating 16 of pressuresensitive adhesive. Since the dressing 10 is able to dissipate fluids that the wound produces, the seal of the dressing around the wound is not undermined by the fluid production of the wound. In the past, this has been a problem with other self adherent, transparent dressings which is a cause for their early removal, sometimes resulting in some damage to the healing wound. The dressing of the present invention can be left in place, and will stay in place, throughout the entire course of the healing process. It is removed only after the wound is healed and is not subject to damage by the adhesive, since normal skin is not damaged by its removal. In accordance with the present invention, the dressing 10 is also transparent for visual inspection of the wound during use of the dressing 10, and as such as the dressing of the wound can be used throughout the entire course of healing. Of course, it is important to inspect the condition of the wound as it proceeds through the healing process in order to check for signs of infection without removing the dressing. The wound may be inspected through the transparent backing 12, the openings 26 of the layer 20, and the apertures 22 of the front sheet 14, even though the adhesive coating 16 may be opaque since the adhesive coating 16 also has apertures 22 in registration with the front sheet 14. A typical example of the present invention is described as follows.

EXAMPLE 1

An elastomer film was used for the backing sheet 12, such as PEBAX film supplied by Schoeller Technical Papers, Pulaski, N.Y., a nylon/polyether block copolymer.

A 170g/yd$^2$ needle punched fabric, 50% rayon, 50% polyester was used for the layer 20, with suitable openings being formed in the layer. An adhesive coated elastomer film highly permeable to water vapor was used for the front sheet 14, such as Polyskin, a trademark of the Kendall Company, Boston, Mass.

Apertures were punched in the adhesive coated front sheet 14 with a ⅛ inch circular punch, with the apertures being on a one inch square grid pattern.

Openings were punched in the layer using a one-half inch circular punch in a gang die to yield holes on a one inch square grid pattern.

The layers were sealed together over the entire surface using a Sentinel pattern sealer.

Figure 4:
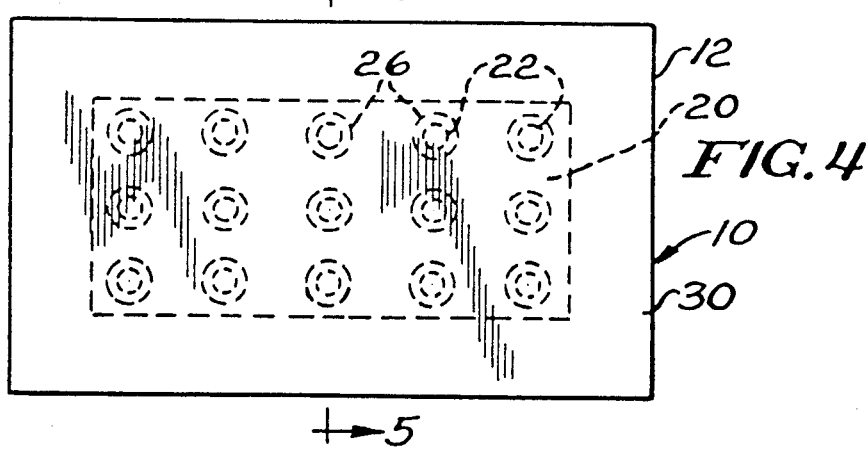
FIG. 4 is a top plan view of another embodiment of a dressing of the present invention.
Figure 5:
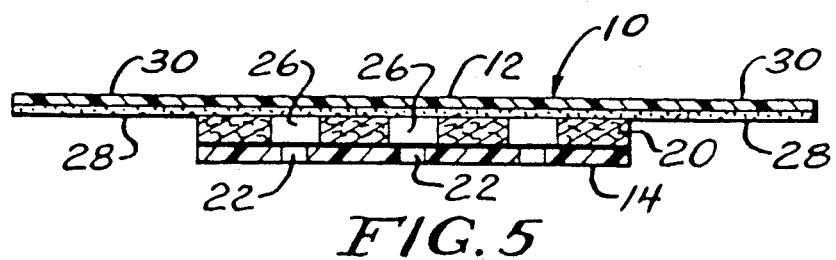
FIG. 5 is a sectional view taken substantially as indicated along the line 5—5 of FIG. 4.

Another embodiment of the present invention is illustrated in FIGS. 4 and 5, in which like reference numerals designate like parts. In this embodiment, the backing sheet 12 has an adhesive coating 28 on a front surface thereof, and the adhesive coating 28 of the backing sheet 12 may be utilized to secure the backing sheet 12 to the layer 20. The backing sheet 12 has side margins 30 extending beyond the periphery of the layer 20 of the front sheet 14 in order to secure the dressing 10 to the skin of a patient peripherally around the dressing 10 while providing a bacterial barrier for the wound around the dressing 10. In this embodiment, the front sheet 14 is free of adhesive. As in other embodiment of the present invention, the dressing 10 also maintains a moist environment for the wound. In other respects, the dressing of FIGS. 4 and 5 is similar to that previously described in connection with FIG. 1-3.

Figure 6:
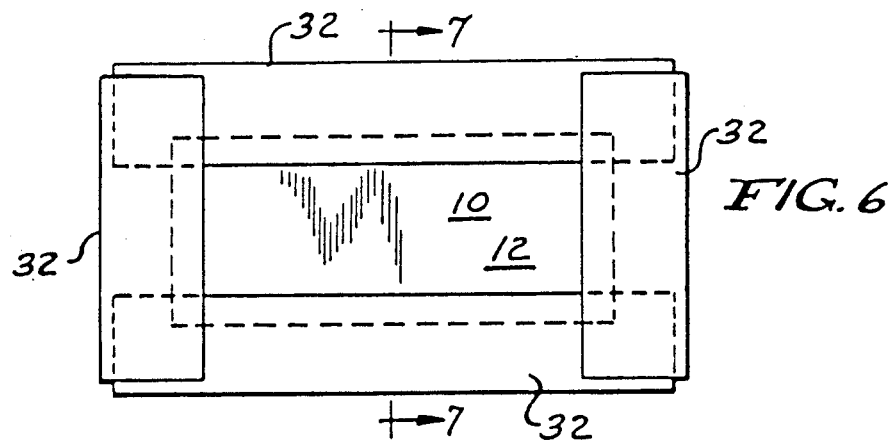
FIG. 6 is a top plan view of another embodiment of a dressing of the present invention.
Figure 7:
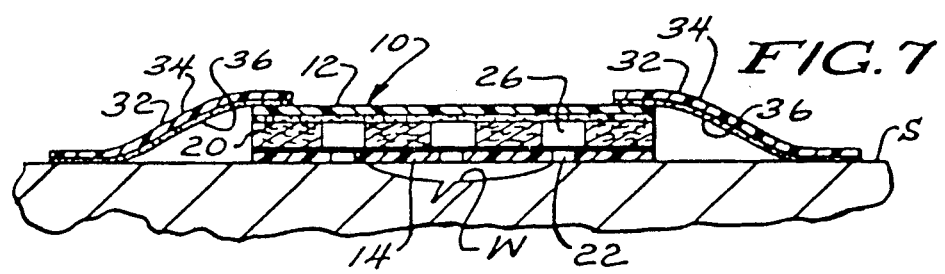
FIG. 7 is a sectional view taken substantially as indicated along the line 7—7 of FIG. 6.

Another embodiment of the present invention is illustrated in FIGS. 6 and 7, in which like reference numerals designate like parts. In this embodiment, the dressing 10 is constructed without side seals, and a plurality of tape strips 32 are utilized to secure the dressing 10 over the wound W peripherally around the dressing 10. The tape strips 12 have a non porous backing 34 which is permeable to water vapor coated with a suitable pressure-sensitive adhesive 36. In this embodiment, the front sheet 14 may be free of an adhesive, and the tape strips may be utilized for any size dressing. The tape strip 32 provides a bacterial barrier for the wound W around the periphery of the dressing 10. In other respects, the dressing 10 of FIGS. 6 and 7 is similar to that previously described in connection with FIGS. 1-3.

Figure 8:
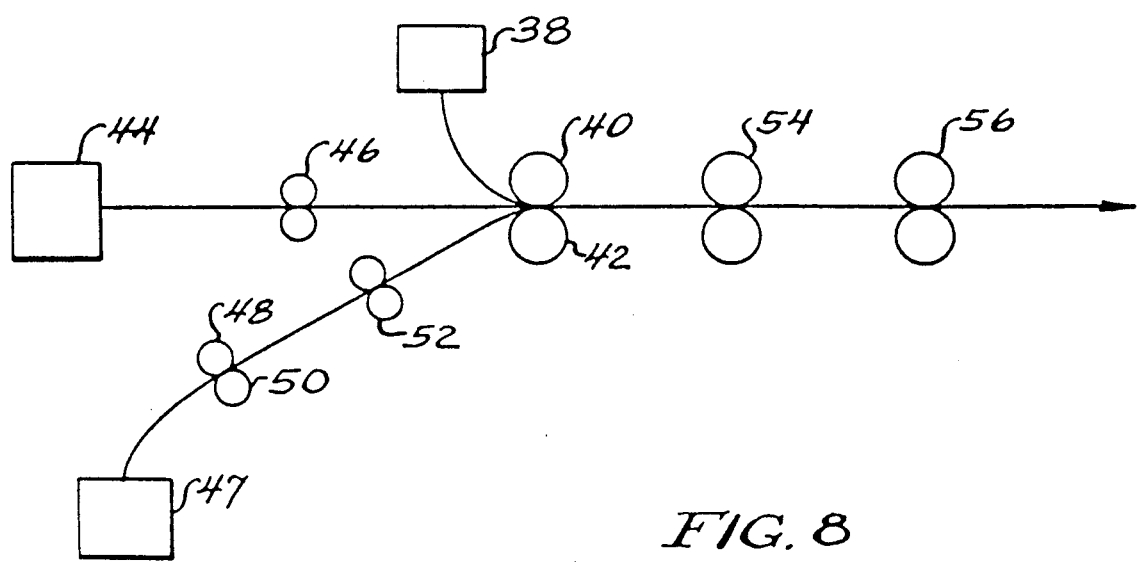
FIG. 8 is a diagrammatic view of an apparatus for making a dressing of the present invention according to a method of the present invention.

An apparatus 37 for constructing a dressing according to the present invention is illustrated in FIG. 8 In this embodiment, a supply 38 of backing sheet 12 is passed through a pair of rollers 40 and 42. A supply 44 of the absorbent layer 20 is passed through a self clearing rotary dye 46 in order to punch the openings in the layer, after which the layer is passed to the rollers 40 and 42. A supply 47 of the front sheet 14 and an adhesive coating 16 is passed through a pair of rollers 48 and 50 to anchor the adhesive to the film, after which the front sheet 14 and adhesive coating 16 is passed to a self clearing rotary punch 52 in order to form the apertures in the front sheet and adhesive coating. The front sheet 14 with adhesive coating is then passed to the rollers 40 and 42. The rollers 40 and 42 are supplied with heat in order to heat seal the front sheet and backing sheet to the absorbent layer, after which the sealed composite is passed through a cutting and sealing device 54 which cuts and seals the dressing perimeter in the machine direction. The dressing is then passed from the cut and seal device 54 to a second cut and seal device 56 which cuts and seals the dressing in the cross direction resulting in the final finished cut dressing. In this manner, the dressing 10 may be constructed by the apparatus of FIG. 8 in accordance with a method of the present invention.

The foregoing detailed description is given for clearness of understanding only, and no unnecessary limitations should be understood therefrom, as modifications will be obvious to those skilled in the art.

What is claimed is:

1. An absorbent dressing comprising:

a transparent backing sheet having a relatively high water vapor permeability;

a front sheet having a pressure sensitive adhesive on a front surface thereof for facing a wound, said front sheet and adhesive having a plurality of apertures in register extending therethrough; and an absorbent layer intermediate the front sheet and backing sheet having a plurality of openings in register with the apertures of the front sheet, with the openings of the layer being at least as large as the apertures of the front sheet.

2. The dressing of claim 1 wherein the openings of the layer are larger than the apertures of the front sheet.

3. The dressing of claim 1 wherein the front sheet and backing sheet are sealed together around their periphery with the layer located inside the seal.

4. The dressing of claim 1 wherein the backing sheet and front sheet are heat sealed to the layer.

5. The dressing of claim 1 wherein the front sheet comprises an elastomer film highly permeable to water vapor.

6. The dressing of claim 1 wherein the backing sheet comprises an elastomer film.

7. The dressing of claim 1 wherein the layer comprises a nonwoven material.

8. The dressing of claim 1 wherein the layer comprises a needle punched fabric.

9. The dressing of claim 1 wherein the lateral dimensions of the dressing are greater than the wound on which it is placed.

10. The dressing of claim 1 including strips of tape having a nonporous highly water vapor permeable backing with an adhesive coating on a front surface thereof, said tape strips securing an edge of the backing sheet to the patient's skin around the periphery of the dressing.

11. The dressing of claim 1 including a release sheet releasably attached on a front surface of the front sheet adhesive.

* * * * *